United States Patent
Sekine et al.

(10) Patent No.: US 6,544,514 B2
(45) Date of Patent: Apr. 8, 2003

(54) COMPOSITIONS COMPRISING, AS THE MAIN INGREDIENT, ALLOGENIC ACTIVATED-C4+ CELLS AND METHOD FOR PRODUCING AND USING THE SAME

(75) Inventors: Teruaki Sekine, 1-13-420, Shiohama 1-chome, Koto-ku, Tokyo (JP), 135-0043; Kiminari Ito, Hokkaido (JP); Kenzo Bamba, Tokyo (JP); Yasuyuki Kuroiwa, Ibaragi-ken (JP)

(73) Assignee: Teruaki Sekine, Tokyo (JP)

( * ) Notice: Subject to any disclaimer, the term of this patent is extended or adjusted under 35 U.S.C. 154(b) by 44 days.

(21) Appl. No.: 09/288,234

(22) Filed: Apr. 8, 1999

(65) Prior Publication Data

US 2002/0001576 A1 Jan. 3, 2002

(30) Foreign Application Priority Data

Apr. 9, 1998 (JP) .......................................... 10-097378

(51) Int. Cl.[7] .................................................. C12N 5/00
(52) U.S. Cl. ...................................................... 424/93.7
(58) Field of Search ...................................... 424/93.71

(56) References Cited

FOREIGN PATENT DOCUMENTS

WO 95 25528 * 9/1995

OTHER PUBLICATIONS

Hirohata et al., J. Immunol. 142(9): 3104–3112 (May 1, 1989).*

* cited by examiner

*Primary Examiner*—Jean C. Witz

(57) ABSTRACT

Compositions or medicaments comprising allogenic activated-CD4+ cells as the main ingredient, which are attributable to an organ or bone marrow transplantation donor, have an extremely beneficial effect for preventing recidivation of a tumor and remedying various infections such as viral infections, and autoimmune diseases such as phagocytosis, without causing any serious GVHD. The allogenic activated-CD4+ cells can be produced by separating lymphocyte cells or CD4+ cells from peripheral blood of the donor or removing CD8+ cells from the peripheral blood of the donor by using anti-CD8+ antibodies to obtain CD4+ cells and proliferating the CD4+ cells thus prepared in proliferation activator.

19 Claims, No Drawings

COMPOSITIONS COMPRISING, AS THE MAIN INGREDIENT, ALLOGENIC ACTIVATED-C4+ CELLS AND METHOD FOR PRODUCING AND USING THE SAME

BACKGROUND OF THE INVENTION

1. Field of the Invention

This invention relates to compositions comprising, as the main ingredient, allogenic activated-CD4+ cells which are derived from a different person, and a method for producing and dispensing the same. More particularly, this invention relates to compositions effective in preventing recidivation of a tumor and remedying various infections such as viral infections, and autoimmune diseases such as phagocytosis.

2. Description of the Related Art

Lymphocytes take part in the immune system concerned in biophylaxis. In particular, T-lymphocytes are one kind of important cells playing a major role in cellular immunity. The lymphocytes are sorted in accordance with the reactivity of the monoclonal antibody. For example, the T-lymphocytes having the reactivity to anti-CD3 antibodies are regarded as CD3+ cells. There have been many studies in the relation between antigens manifested in the lymphocytes and its function. The T-lymphocyte manifests not only the CD3 antigen, but also other antigens of various kinds at the same time. The lymphocytes manifesting CD4 antigens (hereinafter referred to as "CD4+ cells") have been considered to have a function of activating lymphocytes manifesting CD8 antigens (hereinafter referred to as "CD8+ cells"). The CD8+ cell has intense cytotoxic activity. However, the T-lymphocytes have various functions, and thus, they have been generally considered to be difficult to sort only in accordance with the manifesting superficial antigen. It has been reported that the CD4+ cells have the cytotoxic activity in, for example, "Cytotoxic Activity of CD4+ T-cells against Autologous Tumor Cells" by Y. Konishi, T. Sekine, T. Takayama, M. Fujii, and T. Tanaka, Jpn J. Cancer, Res., Vol.86, pp.854–860 (1995).

T. Sekine, one of the inventors of the present invention, disclosed that the lymphocytes can be proliferated by solid-phase anti-CD3 antibody and interleukin-2, and autologous lymphocytes thus proliferated have an antitumor effect (Japanese Patent Application Public Disclosure No. HEI 3-80076(A)). There have been many other reports that the lymphocytes derived from peripheral blood and so on can be proliferated by the anti-CD3 antibody and interleukin-2, and the autologous lymphocytes have antitumor activity.

Ito et al., ones of the inventors of the present invention, reported that the autologous lymphocytes proliferated from the anti-CD3 antibody and interleukin-2 are effective in the treatment of viral infections of a sufferer from congenital immunodeficiency ("Course of Medicine" by Kiminari Ito and Teruaki Sekine, Vol.181, No.6, pp.426–427 (1997)).

A bone-marrow transplant is performed when leukocyte blood types (hereinafter called "HLA" for short) of both donor and recipient agree therewith. However, because various types of HLA are in existence, it is exceedingly rare for the HLA types of the donor and recipient to agree with each other. Accordingly, when the major components of HLA of the donor are in agreement with those of the recipient, the bone-marrow transplant is generally carried out. Failure of complete agreement of the HLA types sometimes causes the graft-versus-host disease (hereinafter called "GVHD" for short) which bring about severe symptoms. For the purpose of remedying the disease, an immunosuppressant has been used. A patient developing the disease may possibly recuperate from GVHD with administration of the immunosuppressant, as a result of which the patient will infrequently manifest viral infections attributable to cytomegalovirus or Epstein-Barr virus and eventually be brought death in most cases.

Elizabeth et al. reported that CD8+ cells specific to cytomegalovirus are derived from lymphocytes of a bone-marrow donor for the purpose of preventing and treating the viral infections caused in the immunosuppressive conditions, so that the viral infections attributable to cytomegalovirus which the recipient is infected with can be treated. (Elizabeth A. Walter, M.D. et al., N. Engl. J. of Med., Vol.333, pp.1038–1044 (1995))

In the actual clinical cases, allogenic lymphocytes prepared by a pheresis operation have been used for the purpose of treating diseases such as leukemia. This treatment is called "donor leukocyte transfusion" (hereinafter called "DLT" for short). DLT shows a beneficial effect, but it has been found that 50% to 80% of acute GVHD or 20% of fatal GVHD emerged in the recipient (H. J. Kolb et al., "Blood", vol.86, pp.2041–2050 (1995); S. Slavin et al., "Exp. Hematol", Vol. 23, pp.1553–1562 (1995)). To make matters worse, it takes several hours to perform the pheresis operation, and the operation imposes a severe burden on the donor.

Giralt et al. reported about DLT using leukocytes excluding CD8+ cells (Giralt et al., "Blood", vol.86, pp.4337–4343 (1995). Ritz et al. reported about DLT using CD4+ cells prepared by a pheresis operation (Claret E. J. et al., "J. Clin. Invest", vol.100, No.4, pp.588–866 (1997)). In either case, it was reported that the effect of GVL (graft-versus-leukemia, a slight case of which favorably reacts on a patient) was derived without causing GVHD, but it is feeble.

The allogenic lymphocytes specific to the antigen are efficacious against the viral infections without causing GVHD. However, the effective spectrum thereof is confined only to the specified viruses. Consequently, the necessity of deriving various types of antigen-specific lymphocytes to cope with various kinds of viral infections arises. In particular, when infections caused by unexpected pathogens such as viruses are developed, the antigen-specific allogenic lymphocytes cannot be used because it takes much time to derive the antigen-specific lymphocytes.

Furthermore, it is difficult to derive the antigen-specific lymphocytes effective for infections in which their pathogenic germs cannot be identified. Thus, there has been a need for allogenic lymphocytes which have wider effective spectrum or are not restricted to the specific effective spectrum.

Administration of the allogenic lymphocytes such as DLT can be expected to produce the intended beneficial curative effect, e.g. antitumor effect, but it consequently increases a possibility of causing serious GVHD with greater frequency. DLT using simply sorted CD4+ cells does not produce GVHD, but has little curative effect. Moreover, DLT necessitates gathering of leukocytes from a donor by the pheresis operation which imposes a severe physical burden on the donor and requires special facilities for fulfilling the operation. Particularly, when the donor is an infant, it is difficult to extract the leukocytes in large quantities therefrom. It has been desired to devise medicaments or preparations which have wide applicability and high efficiency, and besides, can be prepared lessening a burden on the donor without using special facilities and applied clinically without causing GVHD.

An object of the present invention is to provide compositions of lymphocytes applicable for remedying various diseases without causing serious GVHD, which have an excellent curative effect of restraining recidivation of a tumor, and remedying viral infections and autommune diseases and can be widely applied to immunological diseases and bring about marked curative effects in performing a specific treatment.

Another object of the invention is to provide a medical kit for preparing, with high efficiency, the compositions of lymphocytes applicable for remedying various diseases without causing serious GVHD, which have an excellent curative effect of restraining recidivation of a tumor, and remedying viral infections and autommune diseases and can be widely applied to immunological diseases.

Still another object of the invention is to provide a method for preparing, with high efficiency, the compositions of lymphocytes applicable for remedying various diseases without causing serious GVHD, which have an excellent curative effect of restraining recidivation of a tumor, and remedying viral infections and autommune diseases and can be widely applied to immunological diseases.

SUMMARY OF THE INVENTION

To attain the objects described above according to this invention, there is provided compositions or medicaments prepared by separating lymphocyte cells or CD4+ cells from a small quantity of peripheral blood of a donor, and proliferating the cells thus prepared, to obtain allogenic activated-CD4+ cells to be contained therein as the main ingredient.

The medicament according to this invention contains, as the main ingredient, the allogenic activated-CD4+ cells and has an excellent curative effect of restraining recidivation of a tumor, and remedying viral infections and autommune diseases without causing serious GVHD.

The allogenic activated-CD4+ cells may be derived from an organ donor or bone-marrow donor.

The medicament according to this invention may contain 90% of allogenic activated-CD4+ cells relative to the total amount of cells in the medicament.

The medicament according to this invention may contain CD8+ cells relative to the total amount of cells in the medicament.

A method for producing the medicaments according to this invention, which contain, as the main ingredient, the allogenic activated-CD4+ cells, comprises separating CD4+ cells from peripheral blood of a donor, and proliferating the cells thus prepared in the presence of a proliferation activator, to obtain allogenic activated-CD4+ cells to be contained therein as the main ingredient.

Another method for producing the medicaments according to this invention, which contain, as the main ingredient, the allogenic activated-CD4+ cells, comprises removing CD8+ cells from peripheral blood of a donor by using anti-CD8+ antibodies, and proliferating the cells thus prepared in the presence of a proliferation activator, to obtain allogenic activated-CD4+ cells to be contained therein as the main ingredient.

Still another method for producing the medicaments according to this invention, which contain, as the main ingredient, the allogenic activated-CD4+ cells, comprises proliferating allogenic lymphocyte cells in the presence of a proliferation activator, and separating activated-CD4+ cells from the allogenic lymphocyte cells by using anti-CD4+ antibodies, to obtain allogenic activated-CD4+ cells to be contained therein as the main ingredient.

A further method for producing the medicaments according to this invention, which contain, as the main ingredient, the allogenic activated-CD8+ cells, comprises proliferating allogenic lymphocyte cells in the presence of a proliferation activator, and separating activated-CD8+ cells from the allogenic lymphocyte cells by using anti-CD8+ antibodies, to obtain allogenic activated-CD4+ cells to be contained therein as the main ingredient.

In any method, interleukin-2 and/or anti-CD3 antibodies may be used as the proliferation activator.

The allogenic activated-CD4+ cells may be derived from an organ donor or bone-marrow donor.

DESCRIPTION OF THE PREFERRED EMBODIMENTS

The allogenic activated-CD4+ cell in the medicament according to the invention is defined as a CD4+ cell derived from a different person other than a recipient and activated with a proliferating activator having a proliferation activity. As the proliferating activator, interleukin-2, anti-CD3 antibodies and the like can be enumerated.

The allogenic activated-CD4+ cells may be derived from any different person. However, in a case that a patient have already been subjected to bone-marrow or organ transplant surgery, the allogenic activated-CD4+ cells are preferably derived from the bone-marrow and/or organ donor from a medical point of view to lessen the risk of GVHD possibly caused by CD8+ cells or the like, prevent recidivation of a tumor, and remedy various infections such as viral infections, and autoimmune diseases such as phagocytosis.

In particular, for the purpose of avoiding the risk of GVHD caused by CD8+ cells or the like, it is preferable to contain 90% or more activated-CD4+ cells in the medicaments of the invention, which contain, as the main ingredient, allogenic activated-CD4+ cells, relative to the total amount of the cells in the medicament. More preferably, the medicaments of the invention have 95% or more activated-CD4+ cells contained therein relative to the total amount of the cells. That is, the medicament containing, as the main ingredient, allogenic activated-CD4+ cells, is desired to not only increase the content of activated-CD4+ cells, but also contain CD8+ cells as little as possible. To put it concretely, it is desirable to reduce the content of CD8+ cells in the medicament to 10% or less, preferably, 5% or less, more preferably, 1% or less relative to the total of cells in the medicament.

The allogenic activated-CD4+ cells contained in the medicament of the invention may assume any formation.

For example, the allogenic activated-CD4+ cells suspended in an adequate solution may be used. The solution containing the allogenic activated-CD4+ cells can desirably be used as an injection or drip-feed solution. Especially, an injection or drip-feed solution, which is prepared by suspending the allogenic activated-CD4+ cells in physiological saline and so on containing 0.01% to 5% of human seralbumin, is more suitable, but this should not be understood as a limitation.

The allogenic activated-CD4+ cells or the preparations containing them, which are produced by the method of this invention, may be frozen and kept in their frozen state so as to be used for remedying or preventing various disease.

When the medicaments according to the invention can desirably be administered to a patient by an intravenous drip, venoclysis, arterial injection, local injection and so on. The desirable dosage of the medical solution varies in accordance with the way or place of the administration thereof. However, it is commonly desirable to administer 50 to 500 ml of the medical solution containing the allogenic activated-CD4+ cells in the aforesaid ratio to the patient. It is preferable that the medical solution is administered one time a day to one time a month. In any event, at least one administration of the medicament containing the allogenic activated-CD4+ cells should be made.

The dosage of the allogenic activated-CD4+ cells contained, as the main ingredient, in the medicament of the invention, may be arbitrarily decided in accordance with the condition of the patient and/or the clinical procedure. In general, $1\times10^2$ to $1\times10^9$ units of allogenic activated-CD4+ cells per kilogram of patient's weight may be used. It is more desirable to determine the dosage of the allogenic activated-CD4+ cells to $1\times10^4$ to $1\times10^8$ units in the light of the curative effect of the preparations.

The allogenic activated-CD4+ cells contained in the preparations according to this invention may contain various genetic factors, or be prepared by being deprived of or mutating intrinsic genetic factors.

Also, the medicaments or preparations according to this invention can be effectively used for preventing or treating various infections in the conditions of immunodeficiency caused by human immunological deficient virus as the result of using the activated-CD4+ cells short of necessary cofactors taking part in virus infections of human immunodeficiency.

The medicaments or preparations according to this invention can be used regardless of whether or not a donor and a recipient agree in HLA with each other.

The medicaments or preparations of the invention can be applied to patients who are subjected to a bone-marrow transplant or the like, and contracting various infectious diseases, cancer, immunodeficiency, autommune diseases or allergosis.

The infectious diseases include viral infections, bacteriosis, mycetogenic infection, protozoiasis infection, clamydial infection, mycoplasma infection, and the like. The viral infections are attributable to cytomegalovirus and Epstein-Barr virus and other possible viruses. That is, the medicaments of the invention can be applied for preventing and treating various viral infections including those infected by herpes simplex virus, herpesvirus such as varicella zoster virus, human leukosis virus, various retrovirus such as human immunological deficient virus. The microbism on which the medicaments of the invention are effective is typified by the infections attributable to *pseudomonas aeruginosa,* methicillin-resistant *staphylococcus aureus,* or the like. In any event, the medicaments and preparations according to this invention are effective on any infections attributable to germs pathogenically affecting humans. Especially, the present invention can be applied for remedying and preventing the infections caused by pathogenic germs which have been unknown or cannot be identified or diseases accompanying the infections.

The cancerous diseases to which the medicaments of the invention can be applied are typified by leukemia. However, the medicaments of the present invention is not applied only to this disease, but effective in remedying various solid carcinoma. Namely, the medicaments and preparations of the invention are effective in not only preventing the recidivation of a tumor, but also remedying the tumor.

The immunodeficiency on which the medicaments of the invention is effective is roughly divided into congenital immunodeficiency and acquired immunodeficiency. The congenital immunodeficiency includes severe combined immunodeficiency, Wiscott-Aldrich syndrome, adenosine deaminase deficiency, and purine nucleotide-phosphorylase deficiency. However, the prescription with the medicaments and preparations of the invention is not limited only to the immunological deficient diseases enumerated herein. The acquired immunodeficiency includes secondary immunodeficiency caused by use of carcinostatic, immunosuppressive agent, steroid or the like. The medicaments of the invention are not only effective on these diseases, but also applicable to patients short or lack of immunological competence against specific viruses.

The autommune diseases are typified by systemic lupus erythematosus, rheumatoid arthritis, Sjogren syndrome, myasthenia gravis, pernicious anemia, Hashimoto disease, and so on. However, the medicaments of the invention is not applicable only to these diseases.

The allergosis includes bronchial asthma, cryptomeria pollinosis, and urticaria. However, the medicaments according to this invention are not applicable only to these allergic diseases, but can be effectively used for remedying or mitigating these and other allergic diseases.

The method for producing medicaments or preparations which contain, as the main ingredient, allogenic activated-CD4+ cells according to the present invention will be described hereinafter.

The allogenic activated-CD4+ cells to be contained therein as the main ingredient are obtained by separating lymphocyte cells from a small quantity of peripheral blood of a donor, and proliferating the cells thus prepared in a test tube. In a different method, the allogenic activated-CD4+ cells may be obtained by separating lymphocyte cells from a small quantity of peripheral blood of a donor, further separating CD4+ cells, and proliferating the cells thus prepared in a test tube in a similar manner.

The extraction of allogenic lymphocyte or CD4+ cells from the donor may be performed any way, for example, by blood collection, pheresis, or other possible operations. Taking into consideration a physical burden imposed on the donor, the method of extracting the lymphocyte cells or CD4+ cells from the peripheral blood of the donor, which can be carried out with ease, is recommendable.

It is desirable to draw blood from the vein of the donor, and add heparin or citric acid to the blood thus drawn to prevent blood coagulation. The blood of the order of 0.01 ml to 100 ml is generally drawn in one blood extraction operation, but the amount of the blood to be drawn is not limited in the invention. Taking into consideration the physical burden of the donor, labors involved in collecting the blood, and troublesome operations for separating the lymphocyte cells, it is desirable to drawn the blood by 5 ml to 10 ml, preferably 10 ml to 20 ml in one blood extraction operation.

The operation for separating the lymphocyte cells from the blood drawn in the aforementioned manner may be accomplished by a known method for separating lymphocyte cells such as a discontinuous density gradient centrifugation method which is performed by using sucrose or lymphocyte separating agents on the market.

The proliferation of the lymphocyte cells or CD4+ cells in the invention may be effected by a known lymphocyte cultivating method. The cultivation method as disclosed in Japanese Patent Application Public Disclosure No. HEI 3-80076(A) is applicable in this invention by way of example, but should not be construed as a limitation.

In view of the efficiency of proliferating the lymphocyte cells or CD4+ cells, the cultivation of the desired cells is preferably effected in the presence of interleukin-2 used as the proliferating activator. It is more desirable to effect the cultivation in the presence of the interleukin-2 and anti-CD3 antibodies. As one measure, the cultivation may be carried into practice by allowing lymphocyte cells floating in a culture medium solution containing interleukin-2 and putting the solution into a culture flask in which the anti-CD3 antibodies assume their solid phase. Also, various kinds of mitogens may be used as required to activate the cultivation of the CD4+ cells.

The type of the anti-CD3 antibodies used in the invention is not limited to a specific antibody, as far as the antibody makes for proliferation and activation of the desired lymphocyte cells. The anti-CD3 antibodies used for stimulating the lymphocyte cells are possibly yielded in organisms or organic cells by use of refined CD3 molecules. However, from the viewpoint of stability and cost, it is advisable to use OKT-3 antibodies marketed by Ortho Pharmaceutical Corp.

To efficiently proliferate the lymphocyte cells with ease, the anti-CD3 antibodies are desired to be solidified. As an instrument for solidifying the antibodies, there may be used a culture flask or vessel of glass, polyurethane, polyolefine, polystyrene or the like. Sterilized cell-culture flasks made of plastic of various sizes have been on the market, and therefore, can be chosen at pleasure.

The solidification of the aforenoted anti-CD3 antibodies is accomplished by pouring the diluent solution of anti-CD3 antibodies into the instrument for solidifying and permitting it to stand at 4° C. to 37° C. for 2 to 24 hours. For the solidification of the anti-CD3 antibodies, the anti-CD3 antibodies are desired to be diluted in a physiological buffer solution such as a sterilized dulbecco phosphate buffer solution to the concentration of 1 to 30 $\mu$g/ml.

After solidifying, the antibodies can be preserved in a cold room or refrigerator (at 4° C.) until using. When, the solution is removed, and if need arises, the solidified antibodies may be rinsed with the physiological buffer solution such as the dulbecco phosphate buffer solution at a normal temperature.

It is further desirable for practicing the invention to use interleukin-2 with the culture medium solution to increase the efficiency of proliferating the lymphocyte cells. The interleukin-2 is desirably used at concentration of 1 to 2000 U/ml in the culture. medium solution. The interleukin-2 on the market may be used. The interleukin-2 is used in the state dissolved in water, physiological saline, dulbecco phosphate buffer solution or a culture solution for cultivating cells, such as RPMI-1640, DMEM, IMDM, and AIM-V, which have been widely used in general. The interleukin-2 once dissolved in the culture solution is desired to be kept cold during storage to be prevented from being degraded in activity.

As the culture medium solution for cultivating the desired cells, there may be used a culture medium derived from a living organism or a culture medium composed by mixing amino acid, vitamins, nucleic acid base and so on with equilibrium salt solution, but these should be understood as limitative as far as the culture medium applied to the invention is suitable for cultivating the cells. For example, as the culture medium, RPMI-1640, AIM-V, DMEM, IMDM or the like are preferable. In particular, the culture medium of RPMI-1640 is most recommendable. The culture medium with addition of normal human serum excels in proliferating effect and can be preferably used. These culture medium applicable to the invention have been on the market.

The cultivation of the desired cells may be fulfilled by a common cell-cultivating method. For example, it can be carried out in a $CO_2$-incubator at a $CO_2$-concentration of 1% to 10%, preferably 5%, at a temperature of 30° C. to 40° C., preferably 37° C. in particular.

The number of days which the cultivation takes is not specifically restricted, but it is desirable to allow 2 to 20 days, preferably 3 to 7 days, for the cultivating process, so as to transmit the stimulative information of the anti-CD3 antibodies to the cells. Within the period for the cultivation, it is best to observe the conditions of the cells under a microscope and take count of the number of cells so as to suitably adjust the amount of the culture medium solution by adding the solution. The proliferation of the cells does not appreciably take place within 1 to 2 days after commencement of the cultivation, but is generally observed about 3 days after the commencement. When the cells are satisfactorily proliferated, the color of the culture medium solution will be changed from orange to yellow. The loadings of the culture medium solution supplementarily added is preferably about 0.1 to 5 times the culture solution initially given. It is better to supplementarily add the culture solution every 1 to 7 days so as not to degrade the culture solution and decrease the activity of the interleukin-2.

The cultivation may possibly be continued without receiving stimulation from the anti-CD3 antibodies after cultivating the lymphocyte cells in the presence of the anti-CD3 antibodies. That is, the cultivation can be continued with an instrument having no anti-CD3 antibodies solidified, such as a cell-culture flask, a roller bottle and a gas-permeable bag for cultivation, until the medicaments are administered to a subject to be treated. It is desirable to carry out the cultivation of the lymphocyte cells under the conditions noted above in the same manner as that using the anti-CD3 antibodies except that the cells do not receive the stimulation from the solidified anti-CD3 antibodies. Timely use of serum-free culture medium in the cultivation provides advantageous high workability, economy, and safety.

When clinically using the medicaments or preparations according to this invention, it is desired to separate the CD4+ cells serving as the main ingredient for the medicaments, and simultaneously, remove CD8+ cells and CD56+ cells which can be expected to cause GVHD to obtain the CD4+ cells of high purity.

The process for separating the CD4+ cells in the invention may be performed before or after the proliferating and activating processes.

The separation of the CD4+ cells may be effected by a method of positively gathering the CD4+ cells and/or a method of removing CD8+ cells and/or CD56+ cells.

Thus, this invention does not contemplate imposing any limitation on the method of separating the CD4+ cells, CD8+ cells and/or CD56+ cells. For example, the CD4+ cells, CD8+ cells and/or CD56+ cells may be used in the state solidified on (bonded with) the surfaces of magnetic beads.

For example, the method of positively separating the CD4+ cells per se are effected by solidifying on or bonding with the surfaces of magnetic beads the anti-CD4 antibodies. As the magnetic beads applied hereto, dynabeads M-450 CD4 antibodies (anti-CD4 antibodies marked by the magnetic beads) such as DB11116 placed on the market by an importer, Veritas Corporation.

The separation of CD4+ cells can be put into practice by a commonly known separation method. Taking the efficiency of separation into consideration, it is desirable to determine the number of magnetic beads for dynabeads M-450 CD4 antibodies to 0.1 to 100 times, preferably 0.1 to 10 times, more preferably 0.5 to 5 times, that of CD4+ cells to be separated. The CD4+ cells to be separated are desired to be reacted with the dynabeads M-450 CD4 antibodies at a temperature within 4° C. to 40° C., taking into consideration the efficiency of reaction and the safety of cells from damage resulting from the reaction. The quantity of the cells subjected to the reaction may desirably be determined within the range of 0.5 to 1000 m/l, preferably 0.5 to 100 ml, more preferably 1 to 10 ml, taking into consideration the handling during separation and aseptic procedures. As on example of a magnet for use in separating CD4+ cells, which is by no means restricted to a specific type, Magnet MPC-1 (DB12001 imported and marketed by Veritas Corportion) may be used. The cultivation of the cells is desired to be carried on a magnetic plate.

The separation method for separation of CD4+ cells by removing CD8+ cells or CD56+ cells may be carried out by use of the anti-CD8 antibodies or the anti-CD56 antibodies solidified (bonded) on the magnetic beads. The number of the anti-CD8 antibodies or CD56 antibodies marked by the magnetic beads is desirably determined to 1 to 1000 times, preferably 1 to 200 times, more preferably 1 to 50 times, that of CD8+ cells or CD56 cells to be removed, taking into consideration of the efficiency of separating CD4+ cells.

The temperature at which CD8+ cells or CD56+ cells to be removed for separating CD4+ cells are reacted with the anti-CD8 antibodies or CD56 antibodies marked by the magnetic beads is desired to be determined to a range within 4° C. to 40° C., taking into consideration the efficiency of reaction and the safety of cells from damage resulting from the reaction.

The quantity of the cells subjected to the reaction to remove CD8+ cells or CD56+ cells may desirably be determined within the range of 0.5 to 1000 ml, preferably 0.5 to 100 ml, more preferably 1 to 10 ml, taking into consideration the handling during separation and aseptic procedures. Similarly to the method of separating CD4+ cells, as on example of a magnet for use in removing the CD8+ cells or CD56+ cells, which is by no means restricted to a specific type, Magnet MPC-1 (DB12001 imported and sold by Veritas Corportion) may be used.

To increase the purity of CD4+ cells to be obtained, the methods for separating CD4+ cells as described above may desirably be adopted separately or in combination. It is expedient to first remove CD8+ cells and CD56+ cells, and thereafter, positively separate the desired CD4+ cells.

As other expedient methods, a panning technique, rosetto technique or column technique may be adopted for separating CD4+ cells. Namely, the separation method is not specifically limited in the present invention, and may of course be of any one.

As described above, the allogenic activated-CD4+ cells according to this invention can be prepared by suitably using one or more solidified carriers of anti-CD4 antibodies, anti-CD8 antibodies and anti-CD56 antibodies, interleukin-2, and anti-CD3 antibodies in combination.

The medicaments of the present invention can be clinically prepared with ease by independently using such reagents as noted above, or providing a medical kit having two or more component ingredients constituting the medicaments of the invention so as to use them in combination.

For example, the medical kit of the invention may be provided by preparing the component ingredients such as the aforesaid solidified carriers of anti-CD4 antibodies, anti-CD8 antibodies and anti-CD56 antibodies, interleukin-2, and anti-CD3 antibodies as each of the reagents of the medicaments of the invention or combined reagents composed of two or more ingredients. By conveniently using the medical kit of the invention, the desired medicaments of the invention can easily be prepared in use.

Next, some embodiments of the present invention will now be described in detail. However, these embodiments are merely illustrative in nature and should not be construed to limit the spirit and scope of the claims.

[Embodiment 1]

(1) Collection of blood from a bone-marrow donor (hereinafer, referred to as "donor" simply):

In a case that a leukemia patient showed serious III-grade GVHD was recognized 35 days after performing a bone-marrow transplantation for receiving the bone marrow having the same blade type extracted from the donor, a mPSL-pulse treatment was performed by administering to the patient 20 mg/kg, 10 mg/kg and 5 mg/kg of m-PSL (made by Solu-Modrol) each for 2 days, and given the patient 3 mg/kg of immunosuppressive agent (Cyclosporin-A made by Sandimun) 7 days after the transplantation, the patient was recovered for a while, but got into post-transplant immunodeficiency. 75 days after the transplantation, the patient contracted interstitial pneumonia, enteronitis, and virus associated hemophagocytic syndrome (hereinafter, referred to as "VHAS" for short) caused by cytomegalovirus, and then, 112 days after the transplantation, the patient contracted pneumonia and VHAS due to chickenpox. Further, the patient repeatedly contracted viremia caused by cytomegalovirus, and again contracted pneumonia and VHAS on the 135th day from the transplantation. So, therapy using allogenic activated-CD4+ cells was introduced for treating the post-transplant immunodeficiency and cytomegalovirus infections. To perform the therapy using allogenic activated-CD4+ cells, 30 ml of peripheral blood was drawn with heparin from the vein of the same donor who gave the patient the bone marrow.

(2) Separation of myelomonocyte from peripheral blood:

A syringe needle of a syringe with which the blood was collected aseptically in a clean bench (S-1100 model made by Showa Science Co., Ltd.) was removed from a barrel of the syringe without touching a joint portion between the needle and barrel of the syringe, and replaced with another 19G×1½" syringe needle marketed by Nipro Co., Ltd.

Into two centrifugation tubes of 50 ml (Product No. 2341-050 made by Iwaki Glass Co., Ltd.), a culture medium (Product No. GM1106 made by Nikken Bio Medical Laboratory) was placed by 15 ml, and then, all the blood collected was poured equally at a slow speed.

After tightly close the centrifugation tubes with lids, the contents in the tubes were mingled by turning the tubes upside down two to three times. Thereafter, 3 ml of Lymphosepar-I (Product No. 23010 made by Immuno Biological Laboratory) was poured into each of six centrifugation tubes of 15 ml in capacity (Product No. 2327-015 made by Iwaki Glass Co., Ltd.) by using a pipette of 10 ml in capacity (Product No. 4105 imported and marketed by Corning Costar Japan Corp.), and then, 10 ml of blood diluted with the culture medium was slowly poured into each of centrifugation tubes so as not to disarrange the surface of the contents in each tube.

The centrifugation tubes thus prepared were mounted in a centrifugal separator (H-700R made by Kokusan Corp.) and subjected to centrifugal separation at 1800 rpm at a centrifugal temperature of 20° C. for 15 minutes in the state of switching off a brake.

After subjecting the centrifugal separation, lymphocyte cells thus separated were slowly sucked up to the height of about 1 cm from a layer of lymphocytes in the centrifugation tube by use of an evacuator in the asepsis state, taking care not to be sucked out. Then, the layer of lymphocyte cells was collected with a pipette of 5 ml in capacity, taking care not to suck a layer of blood clots, to the centrifugation tube of 50 ml in capacity into which 25 ml of rinsing culture medium (RPMI1640+6) was placed in advance. The centrifugation tube closed with a lid was turned upside down two to three times, and then, subjected to centrifugal separation at 1800 rpm at a centrifugal temperature of 20° C. for 10 minutes.

Upon completion of the centrifugal separation, supernatant liquid in the centrifugation tube was removed, and sedimentum of cells was stirred by using a vortex to be thoroughly loosened. Further, after adding 50 ml of rinsing culture medium therewith and well turning it upside down, there were sampled 500 $\mu$l of cell suspension for measuring the number of cells with a micro tube of 10 ml in capacity, and 500 $\mu$l of cell suspension for measuring the contents of CD4 and CD8 with a micro tube of 1.5 ml in capacity (Model 72.690 imported and marketed by Assist Co., Ltd.)

(3) Measurement of the number of cells with Turk's solution:

With 40 $\mu$l of Turk's solution made by Muto Pure Chemicals Co., Ltd., 10 $\mu$l of the cell suspension for measuring the number of cells, which was obtained in the aforementioned process (2) of separating myelomonocyte, was mixed, and then, 10 $\mu$l of the mixture thus obtained was applied to a hemocytometer (Model 9731 made by Perkin-Elmer Corp.) and observed by a microscope (Model 211320 made by Olympus Optical Co., Ltd.) to count the cells. Consequently, $8.5\times10^7$ of cells in total were counted out.

(4) Analysis of CD4+ cells:

Two samples of the cell suspension obtained in the aforementioned process (2) of separating myelomonocyte were subjected to centrifugal separation at 6000 rpm at 4° C. for 5 minutes to precipitate the cells with a centrifugal separator (Model M-150 made by Sakuma Seisakusho Co., Ltd.).

After removing the supernatant liquid from the samples, 8 $\mu$l of Dulbecco phosphate (made by Nipro Co., Ltd. and hereinafter, referred to as "PBS" for short) and 8 $\mu$l of CD4/CD8 antibodies (Product No. 340039 imported and marketed by Nippon Becton Dickinson Co., Ltd.) were poured into each tube, stirred well, and reacted at 4° C. for 30 minutes.

After the reaction, each sample thus obtained was stirred with 800 $\mu$l of sheath solution (Isoton II made by Coulter Inc.) in each tube by use of a vortex, and then, subjected to centrifugal separation at 6000 rpm at 4° C. for 5 minutes to precipitate the cells. Thereafter, upon clearly removing the supernatant liquid from each sample, 800 $\mu$l of sheath solution was further added, subjected to pipetting to loose the cells, and placed in a tube for measuring FACS (Product No. 2052 imported and marketed by Nippon Becton Dickinson Co., Ltd.)

As the aforementioned FACS, there was used FACScan which has been imported and marketed by Nippon Becton Dickinson Co., Ltd. Measurement of FACS was carried out in accordance with a manual attached to the product.

As the result of measurement, 28% of CD4+ cells and CD8+ cells were found to be contained, respectively. From the FACS Analysis based on the total number of cells measured in the measurement, the respective number of CD4+ cells and CD8+ cells could be concluded to be $2.4\times10^7$.

(5) Preparation of OKT3-solidifying flasks of middle size and large size:

Into a culture flask of middle size (Product No. MS-2125R made by Sumitomo Bakelite Co., Ltd.), 5 ml of a solution of OKT3 (produced by Ortho Pharmaceutical Corp. and imported and marketed by Janssen-Kyowa Co., Ltd.) prepared with PBS(-) to 5 $\mu$g/ml was poured, and into a culture flask of large size (Product No. MS-2080R made by Sumitomo Bakelite Co., Ltd.), 10 ml of the solution of OKT3 was poured. The solutions poured were made even on the bottom of each flask and preserved in a cold room until usage.

(6) Preparation and cultivation of CD4+ cells by use of anti-CD8 antibodies marked by magnetic beads:

From 50 ml of cell suspension prepared in the aforementioned process (2) of separating myelomonocyte touched upon above, 20 ml of cell suspension, which contains $3.4\times10^7$ in total cells including CD4+ cells of $9.5\times10^6$ and CD8+ cells of $9.5\times10^6$, was taken out, and poured into a tube of 50 ml in capacity, and then, subjected to centrifugal separation at 1000 rpm at a centrifugal temperature of 20° C. for 10 minutes.

After the centrifugal separation process, supernatant liquid was removed, and sedimentum of cells was stirred by using a vortex to be thoroughly loosened.

Into a tube of 15 ml in capacity (Model 62.553.002S imported and marketed by Assist Co., Ltd.), 300 $\mu$l of solution of anti-CD8 antibodies marked by magnetic beads (DB11108 imported and marketed by Veritas Corporation) was poured. Upon mounting the tube onto Magnet MPC-1 (Product No. DB12001 imported and marketed by Veritas Corporation), reaction thereof was carried out for 5 minutes. Thereafter, the solution was taken out without sucking the beads, and then, the tube was demounted from the Magnet.

Into the tube, 1 ml of PBS(-) solution was poured, and the tube was well stirred and mounted onto the Magnet. After reacting the solution for 1 minute, the solution was taken out without sucking the beads, and then, the tube was demounted from the Magnet.

Once more, 1 ml of PBS(-) solution was poured into the tube, and the tube was well stirred and mounted onto the Magnet. After reacting the solution for 1 minute, the solution was taken out without sucking the beads, and then, the tube was disconnected from the Magnet.

To the cell suspension collected by the centrifugal separation process, 5 ml of reacting culture medium prepared by combining 45 ml of rinsing culture medium and 5 ml of human serum was added. Upon slightly stirring the solution to suspend the cells therein, the cells were placed into a tube containing anti-CD8 antibodies marked by magnetic beads, and then, reacted for 30 minutes in a cold room while being lightly shaken by using a mild mixer (Model PR-12 made by Taitec Corp.)

After reaction, the tube was mounted to the Magnet, and the solution containing the cells was reacted for 1 minute. Then, the solution was taken out without sucking the beads and moved to another tube of 15 ml in capacity. Again, the tube was mounted to the Magnet, and the solution containing the cells was reacted for 1 minute, and thereafter, the solution was taken out without sucking the beads and moved to still another tube. Then, the solution was subjected to centrifugal separation at 1000 rpm at a centrifugal temperature of 20° C. for 10 minutes. After the centrifugal separation process, supernatant liquid was removed, and sedimentum of cells was stirred by using a vortex to be thoroughly loosened.

To the CD4+ cells thus collected, 20 ml of cultivating culture medium, which is prepared by mixing 44 ml of culture medium (PRPMI1640+7 made by Immuno Biological Laboratory), 1 ml of 35,000 U/ml-IL-2 made by Cetus Corporation, and 5 ml of human serum, was added, and slightly stirred to suspend the cells in the solution.

The solution of OKT3 prepared in the OKT3-solidifying culture flask of middle size in the same manner as that in the aforementioned process (5) of preparing the OKT3-solidifying flasks was sucked up by using an evacuator. Upon pouring 10 ml of PBS(−) into the flask, the flask closed with a lid was hard shaken, and thereafter, upon opening the lid, the solution was thrown away.

Again, upon pouring 10 ml of PBS(−) into the flask in the clean bench, the flask was closed with the lid and hard shaken, and thereafter, upon opening the lid, the solution was thrown away. Then, the remaining solution in the flask was carefully sucked up by using the evacuator.

To the flask thus kept clean, the cell suspension was moved, and then, there were prepared one sample of 10 $\mu$l of the cell-suspended solution for measuring the number of cells, and two samples of 1000 $\mu$l of the solution for measuring the contents of CD4+ cells and CD8+ cells, which were made by pouring 500 $\mu$l of the solution into each tube of 1.5 ml in capacity. The samples were placed in a $CO_2$-incubator (Sterile-cult Incubator MIP-3033 made by Sanyo Electric Co., Ltd.) to cultivate the cells at 37° C. at a humidity of 95% (the first day of the cultivation). Analysis of the CD4+ cells was made in the aforementioned analyzing process of CD4+ cells.

The result of the analysis revealed that the content of CD4+ cells is 46%, and that of CD8+ cells is 5%.

(7) Measurement of the number of cells by use of trypan blue solution:

With 20 $\mu$l of trypan blue solution (Product No. T-8154 imported and marketed by Sigma-Aldrich Japan K.K.), 10 $\mu$l of cell-suspended solution sampled for measuring the number of cells in the aforementioned process (6) for preparing and cultivating CD4+ cells was mixed, and then, 10 $\mu$l of the mixture was applied to a hemocytometer (Model 9731 made by Perkin-Elmer Corp.) and observed by a microscope (Model 211320 made by Olympus Optical Co., Ltd.) to count the cells. Consequently, $2.6 \times 10^7$ of cells in total were counted out.

(8) Expansive cultivation of CD4+ cells:

To the cell solution cultivated in the aforementioned process (6) for cultivating CD+4 cells, 25 ml of cultivating culture medium was added respectively on the 3rd and 4th days from the commencement of cultivation.

The OKT3-solidifying flask containing the culture medium and CD4+ cells was replaced by another flask of large size to increase the quantity of the cells being cultivated on the 5th day. To be more specific, the solution of OKT3 prepared in the OKT3-solidifying culture flask of large size in the same manner as that in the aforementioned process (5) of preparing the OKT3-solidifying flasks was sucked up by using the evacuator, and then, upon pouring 50 ml of PBS(−) into the flask, the flask closed with a lid was hard shaken, and thereafter, upon opening the lid, the solution was thrown away.

Again, upon pouring 50 ml of PBS(−) into the flask in the clean bench, the flask was closed with the lid and hard shaken, and thereafter, upon opening the lid, the solution was thrown away. Then, the remaining solution in the flask was carefully sucked up by using the evacuator.

To the flask of large size thus rinsed out, the cell suspension solution clinging to the bottom of the flask of middle size was transferred by lightly tapping the flask several times to tear off the cell suspension from the bottom of the flask.

Further, 50 ml of cultivating culture medium solution was poured into the flask of middle size, and then, upon shaking the flask to suspend the cells in the culture medium solution poured thereinto, the culture medium solution in which the cells are suspended was transferred in the flask of large size. Thereafter, the cultivation of the cells were continued in the flask of large size at 37° C. in the $CO_2$-incubator.

(9) Freezing preservation of CD4+ cells:

To the cell solution cultivated in the process (8) for expansively cultivating CD4+ cells, a part of the cell solution were frozen to be preserved on the 6th day from the commencement of cultivation. The freezing of the cells was carried out by lightly tapping the flask several times to tear off the cells clinging to the bottom of the flask. Then, 500 $\mu$l of the culture solution was taken out from the flask, strewn on agar of trypto soy (TSA) (Product No. P94501 made by Immuno Biological Laboratory), and subjected to an aseptic test in the $CO_2$-incubator (Model SLI-450 made by Tokyo Rikakikai Corp.)

From the flask, 10 $\mu$l of culture solution was taken out to count the number of cells in the same manner as done in the aforementioned process (3).

Next, the cells cultivated were poured by 40 ml into two tubes each having a capacity of 50 ml and subjected to centrifugal separation at 1000 rpm at 20° C. for 5 minutes. After the centrifugal separation process, supernatant liquid was removed, and sedimentum of cells was stirred by using a vortex. After the cell suspension solution, 5 ml of cell-preserving solution prepared by mixing 5 ml of human serum, 5 ml of dimethyl sulfoxide (called "DMSO" made by Nakarai Tesque Inc.) and 40 ml of culture medium solution (RPMI1640+7) were respectively cooled in ice for 5 minutes, the cell suspension solution was poured into one flask along with 5 ml of cell-preserving solution and subjected to pipetting to make the cells uniform in the solution. The solution thus obtained in one flask was equivalently divided into three cell-preserving tubes each having a capacity of 2.0 ml (Product No. 430289 imported and marketed by Corning Costar Japan Corp.).

Further, the tubes were placed in a bicell (made by Nippon Freezer Company) and preserved at −80° C. for several days, and thereafter, stored in a liquid nitrogen tank (Model XC47/11 made by Minnesota Valley Engineering).

The concentration of cells during cultivation was $9 \times 10^6$ U/ml, and the number of cells stored was $51 \times 10^7$ per tube.

(10) Taking-out and revitalization of frozen CD4+ cells:

One sample of CD4+ cells stored in the frozen state in the aforementioned process (9) was taken out and warmed at 37° C. for 4 minutes by a heat block (Model TAL-1G made by Taitec Corp.)

To a centrifugation tube having a capacity of 15 ml, 10 ml of cultivating culture medium (RPMI1640+6) was poured in an asepsis state, and lymphocyte cells stored were added thereto with a transfer pipette (Model 86.1172.001 imported and marketed by Assist Co., Ltd.) and caused to be suspended in the solution.

After subjecting the solution at 1000 rpm at 20° C. for 5 minutes, supernatant liquid was removed, and the tube was lightly tapped to suspend the cells in 50 ml of cultivating culture medium. Then, the cell-suspended solution was transferred to a cloning plate (Product No. 704160 made by Greiner Laboratory).

After observing the cells by use of a microscope, the cells were placed in the $CO_2$-incubator to start cultivation at 37° C. (the first day of the cultivation).

On the 2nd day from the commencement of cultivation, the cells were confirmed to proliferate all over the cloning plate by use of the microscope, and then, the cells proliferated on the cloning plate transferred to a flask having a capacity of 225 cm(2) (225 cm(2)-cell Culture Flask imported and marketed by Corning Costar Japan Corp.).

To the cloning plate, 50 ml of new culture medium for cultivating the cells was added. The cells were transferred to another flask upon rinsing and continued to cultivate at a cultivating temperature of 37° C. in the $CO_2$-incubator.

On the 4th day from the commencement of cultivation, the solution of OKT3 prepared in the OKT3-solidifying culture flask in the same manner as that in the aforementioned process (5) of preparing the OKT3-solidifying flask of large size was sucked up by using an evacuator. Upon pouring 50 ml of PBS(−) into the flask, the flask closed with a lid was hard shaken, and thereafter, upon opening the lid, the solution was thrown away by use of a decanter. Then, the remaining solution in the flask was carefully sucked up by using the evacuator.

To new flask thus rinsed out, the cell suspension solution clinging to the bottom of the source flask was transferred by lightly tapping the flask several times to tear off the cell suspension from the bottom of the source flask. Further, 150 ml of cultivating culture medium solution was poured into the new flask of middle size, and then, upon shaking the new flask to suspend the cells in the culture medium solution poured thereinto, the culture medium solution in which the cells are suspended was transferred into the new flask. Thereafter, the cultivation of the cells in the new flask was continued at 37° C. in the $CO_2$-incubator.

(11) Cultivation of CD4+ cells in a cultivating bag:

On the 6th day from the commencement of cultivation, the flask in which the cells are cultivated was tapped several times to tear off the cells clinging to the bottom of the flask. Then, 1 ml of the culture solution was taken out from the flask, equivalently strewn on chloramphenicol-added Sabouraud's dextrose agar (Product No. P93101 made by Immuno Biological Laboratory) and sheep blood agar (Product No. P96201 made by Immuno Biological Laboratory), respectively, and subjected to an aseptic test at 37° C. in the $CO_2$-incubator.

Upon taking out 10 μl of culture solution from the flask, the number of cells in the culture solution was counted in the same manner as that in the aforementioned process (7). A culture bag A-1000 (cell-cultivating bag sold by Nipro Co., Ltd.) containing AIM-V culture medium prepared for bag-cultivation, which is prepared by equivalently adding, to culture medium 087-0112BK imported and marketed by GIBCO-BRL Life Technologies Inc., IL-2, human serum and oxaloacetic acid at the final rate of 200 U/ml, 1% and 1 mM respectively relative to the final concentration of the solution, was warmed at 37° C.

The culture bag was aseptically connected to a 50 ml-syringe (Model 08-912-01 sold by Nipro Co., Ltd.), and all the culture solution in the flask was poured through the syringe.

A tube was sealed at its both end with tube sealer (made by SEBRA) while being held by a forceps, and then, the bag was placed in the $CO_2$-incubator (Model CPD-300A made by Hirasawa Works) to continue the cultivation at a cultivating temperature of 37° C.

(12) Aseptic test and endotoxin assay of CD4 cells:

On the 7th day from the commencement of cultivation (the day before administration), from the culture bag in which the cells have been cultivated in the aforementioned process (11), 1 ml of the culture solution was aseptically sampled by using a 1 ml-syringe (Model 08-010-4 sold by Nipro Co., Ltd.) provided with a 24G×1"-syringe needle (sold by Nipro Co., Ltd.) through a sampling port in the culture bag.

The solution first taken out was thrown away, 1 ml of solution secondarily taken out in the same manner. Of the solution taken out, 200 μl of solution was strewn on sheet blood agar, and remaining solution was poured into a dry-heat sterilization tube (Model 800800 made by Seikagaku Corp.). The sampling port in the bag upon completion of taking out the solution was well wiped with alcohol-contained cotton held by a forceps, and closed with a lid, and thereafter, warmed at a cultivating temperature of 37° C. in the $CO_2$ incubator to continue the cultivation.

The agar plate used in the cultivation was placed in the incubator kept at 37° C. to perform an aseptic test, and the dr-heat sterilization tube was subjected to centrifugal separation at 1000 rpm at 20° C. for 5 minutes.

The ready-made chief solution, which was prepared by using an endotoxin-countering kit, TOXICOLOR LS-200 set (Product No. 010135 made by Seikagaku Corp.), and another endotoxin-countering kit, TOXICOLOR ET-1 set (Product No. 010035 made by Seikagaku Corp.), was poured by 100 μl into each of three dry-heat sterilization tubes (Product No. 800801 made by Seikagaku Corp.) by use of a disposable dry-heat sterilizing micro pipette (Product No. 800801 made by Seikagaku Corp.).

There were poured 100 μl of distilled water for injection (sold by Otsuka Pharmaceutical Co., Ltd.) into a blank test tube, and 100 μl of standard solution to a positive-controlling test tube, respectively, by use of the disposable dry-heat sterilizing micro pipette.

Into a sampling test tube, 80 μl of distilled water for injection and 20 μl of supernatant liquid of the centrifugally separated culture solution were poured by use of the disposable dry-heat sterilizing micro pipette. The samples in the three test tubes were reacted at 37° C. for 30 minutes in a water bath (Model RACOM-ACE HT-80 made by Iuchi Seieido Co., Ltd.).

Into each of the test tubes, 400 μl of 0.8 M acetic acid solution (special grade acetic acid made by Wako Pure Chemical Industries, Ltd.) was poured. Upon shaking the test tubes by use of a vortex, 400 μl of reacted solution was transferred to each of 96-well-micro titer plates (Product No. MS-8096F made by Sumitomo Bakelite Co., Ltd.), and measured at absorbancy index of 405 nm (reference 630 nm) by using a plate reader (Model ETY-96 made by Toyo Sokki Inc.) Consequently, it was confirmed that the absorbance even five times that of the specimen did not exceed the value for positive controlling.

(13) FACS analysis of CD4+ cells for administration before collection:

Before collecting CD4+ cells, the culture solution cultivated in the bag was sampled in part to measure the number of cells in the same manner as that in the aforementioned process (7) and the content of CD8+ cells in the same manner as that in the aforementioned process (4).

As a result, it was found that the culture solution under test contained $3.0 \times 10^9$ of cells in total and 6% of CD8+ cells. From the total number of the cells and the percentage of the CD8+ cells as the result of the FACS analysis, the number of CD8 cells could be calculated to $1.8 \times 10^8$. Hence, it was tried to further remove CD8+ cells by utilization of anti-CD8 antibodies marked by magnetic beads before administering the cells to a patient.

(14) Preparation and collection of CD4+ cells with anti-CD8 antibodies marked by magnetic beads:

Into two centrifugation tubes (Model 25350-250 imported and marketed by Corning Coster Japan Corp.), 250 ml of culture solution cultivated in the bag was poured respectively and subjected to centrifugal separation at 1500 rpm at 20° C. for 8 minutes.

After the centrifugal separation, supernatant liquid in the centrifugation tube was removed, and the remaining culture solution was again subjected to centrifugal separation at 1500 rpm at 20° C. for 8 minutes.

Upon completion of the centrifugal separation, supernatant liquid in the centrifugation tube was removed once more, and stirred by using a vortex to thoroughly loosen cell sedimentum. Next, 250 ml of cell-rinsing fluid, which was prepared by pouring 4.5 ml of 20%-human seralbumin solution (10-17-S(1000 ml) produced by Nihon Pharmaceutical Co., Ltd.) into a bag containing physiological saline by use of a 5 ml-syringe with a 19G-needle (SS-05S produced by Terumo Corp.), was poured into each of the centrifugation tubes, and subjected to centrifugal separation at 1800 rpm at 20° C. for 8 minutes.

After the centrifugal separation, supernatant liquid in the centrifugation tube was removed, and and stirred by using a vortex to thoroughly loosen cell sedimentum.

Into each of the tubes of 50 ml in capacity, 10 ml of cell-rinsing solution was poured respectively.

Into two tubes of 15 ml in capacity, 5 ml of anti-CD8 antibodies marked by magnetic beads four times in number CD8+ cells were poured by the same quantity. The tubes containing the anti-CD8 antibodies were mounted onto the Magnet MPC-1 to react for 1 minute.

Upon taking out solution from each tube without sucking the beads, the tubes were disconnected from the Magnet. Into each tube, 1 ml of PBS(−) solution was poured, and the tube was well stirred and mounted onto the Magnet. After reacting the solution for 1 minute, the solution was taken out without sucking the beads, and then, the tube was disconnected from the Magnet.

Once more, 1 ml of PBS(−) solution was poured into each tube, well stirred and mounted onto the Magnet. After reacting the solution for 1 minute, the solution was taken out without sucking the beads, and then, the tube was disconnected from the Magnet.

Into each tube, 10 ml of cells suspension solution prepared in the foregoing manner was poured and slightly stirred to suspend the cells in the solution, and then, reacted for 30 minutes in a cold room while being lightly shaken by using the mild mixer.

After reaction, each tube was mounted to the Magnet, and the solution containing the cells was reacted for 1 minute. Then, the solution was taken out without sucking the beads and moved to another tube of 15 ml in capacity.

Again, the tube was mounted to the Magnet, and the solution containing the cells was reacted for 1 minute, and thereafter, the solution was taken out without sucking the beads and moved to still another tube. Then, the solution was subjected to centrifugal separation at 1000 rpm at a centrifugal temperature of 20° C. for 10 minutes. After the centrifugal separation process, supernatant liquid was removed, and sedimentum of cells was stirred by using a vortex to be thoroughly loosened.

After well suspending the cell suspension in a final solution (solution to be administered to a patient, which is mixed with 200 ml of physiological saline and 20% of human seralbumin in a centrifugation tube), the solution was filtrated through 100-micron mesh (Product No. 2350 imported and marketed by Nippon Becton Dickinson Co., Ltd.), and then, the quantity of the cell suspension solution was measured.

Further, the cell suspension solution was sampled to measure the number of cells in the solution and the content of CD4.

A 50 ml-syringe was connected to a separation bag T-030 (Product No. BB-T030CJ(300 ml) produced by Terumo Corp.) through a tube to introduce the cell suspension solution into the bag through the syringe. After introduction of the cell suspension solution into the bag, a plunger of the syringe was pressed into the syringe barrel to squeeze out the remaining solution in the syringe, and then, the tube connecting the syringe to the bag was pinched by a forceps and sealed with a tube sealer, consequently to be cut with scissors.

As the result of measurement, the quantity of the solution was 200 ml, and the number of cells in total was $8.0 \times 10^8$.

(15) FACS analysis of CD4+ cells for administration after collection:

FACS analysis of CD4+ cells to be administered to a patient were carried out after collecting the cells in the same manner as that in the aforementioned process (4). As the result of the analysis, the content of CD4+ cells was 99%, and the content of CD8+ cells was 1%.

(16) Administration of CD4+ cells to a patient:

The CD4+ cells prepared in the aforementioned process (14) were administered to a patient through the vein of the patient over a period of 1 hour at a rate of $3 \times 10^7$ U/kg per patient weight.

[Embodiment 2]

(1) Taking-out and revitalization of CD4+ cells in store:

One of the flasks preserved in the frozen state in the process (9) of the foregoing Embodiment 1 was picked out to be revitalized in the same manner as that of the aforementioned process (10) of the foregoing Embodiment 1.

(2) Preparation and cultivation of CD4+ cells by use of anti-CD8 antibodies marked by magnetic beads and anti-CD4 antibodies marked by magnetic beads:

On the 3rd day from the commencement of the cultivation, the cells cultivated in the aforementioned process (1) were first reacted with anti-CD8 antibodies marked by magnetic beads in order to pick out more pure CD4+ cells. So, negative fraction was collected, and reacted with the anti-CD8 antibodies marked by magnetic beads to be cultivated.

To be more specific, a part of the culture solution in which the cells were cultivated was sampled to measure the number of the cells in the same manner as that in the process (3) of Embodiment 1 described above, and measure the contents of CD4+ cells and CD8+ cells in the solution in the same manner as that in the process (4) of Example 1.

As a result, it was found that the concentration of cells was $7.8 \times 10^5$ U/ml, and the contents of CD8+ cells and CD4+ cells were 5.2% and 86%, respectively.

Thereupon, CD4+ cells were prepared from 25 ml of culture solution containing $2 \times 10^7$ of cells by using 15 μl of anti-CD8 antibodies marked by magnetic beads in 1 ml of culture medium solution containing the magnetic beads and CD8+ cells in the ratio of 1:1 in number, in the same manner as that of the process (6) of Embodiment 1.

Next, into new tube of 15 ml in capacity (Product No. 62.553.002S imported and sold by Assist Co., Ltd.), 121 µl of anti-CD4 antibodies marked by magnetic beads (Product No. DB12001 imported and sold by Veritas Corporation) containing CD4+ cells and beads of the same number was poured, and then, the tube was mounted onto Magnet MPC-1 (Model DB12001 imported and sold by Veritas Corporation) to react the solution for 1 minute. Thereafter, the solution. was taken out without sucking the beads, and then, the tube was demounted from the Magnet.

Into the tube, 1 ml of PBS(−) solution was poured, and the tube was well stirred and mounted onto the Magnet. After reacting the solution for 1 minute, the solution was taken out without sucking the beads, and then, the tube was demounted from the Magnet. Once more, 1 ml of PBS(−) solution was poured into the tube, and the tube was well stirred and mounted onto the Magnet. After reacting the solution for 1 minute, the solution was taken out without sucking the beads, and then, the tube was disconnected from the Magnet.

The cell suspension containing the CD4+ cells prepared by using anti-CD8 antibodies marked by magnetic beads were placed into a tube containing anti-CD4 antibodies marked by magnetic beads, and then, reacted for 30 minutes in a cold room while being lightly shaken by using the mild mixer (Model PR-12 made by Taitec Corp.).

Thereafter, the tube from which the solution was taken out without sucking the beads was demounted from the Magnet, and then, upon pouring 5 ml of culture medium for reaction into the tube, it was lightly stirred and mounted onto the Magnet. After reacting the solution for 1 minute, the solution was taken out without sucking the beads, and then, the tube was disconnected from the Magnet. Thereupon, 10 ml of culture medium for cultivation was added to CD4+ cells to be lightly suspended.

The solution of OKT3 prepared in the OKT3-solidifying culture flask of middle size in the same manner as that in the aforementioned process (5) of Embodiment 1 was sucked up by using an evacuator. Upon pouring 10 ml of PBS(−) into the flask, the flask closed with a lid was hard shaken, and thereafter, upon opening the lid, the solution was thrown away. Again, upon pouring 10 ml of PBS(−) into the flask in the clean bench, the flask was closed with the lid and hard shaken, and thereafter, upon opening the lid, the solution was thrown away. Then, the remaining solution in the flask was carefully sucked up by using the evacuator.

To the flask thus kept clean, the cell suspension was moved, and then, continued to cultivate the cells at 37° C. at a humidity of 95% (the first day of the cultivation) in a $CO_2$-incubator (Sterile-cult Incubator MIP-3033 made by Sanyo Electric Co., Ltd.) on the 3rd day from the commencement of cultivation.

On the 5th day from the commencement of cultivation, the solution of OKT3 prepared in the OKT3-solidifying culture flask of. large size in the same manner as that in the aforementioned process (5) of Embodiment 1 was sucked out by using the evacuator, and then, upon pouring 50 ml of PBS(−) into the flask, the flask closed with a lid was hard shaken, and thereafter, upon opening the lid, the solution was thrown away.

Again, upon pouring 50 ml of PBS(−) into the flask in the clean bench, the flask was closed with the lid and hard shaken, and thereafter, upon opening the lid, the solution was thrown away. Then, the remaining solution in the flask was carefully sucked up by using the evacuator.

To a tube of 15 ml in capacity, the cell suspension solution clinging to the bottom of the flask of middle size was transferred by lightly tapping the flask several times to tear off the cell suspension from the bottom of the flask. The tube was mounted onto the Magnet to react the solution for 1 minute.

The cell suspension solution was taken out without sucking the beads and moved to another tube of 15 ml in capacity.

Again, the tube was mounted to the Magnet, and the solution containing the cells was reacted for 1 minute, and thereafter, the solution was taken out without sucking the beads and moved to another OKT3-solidifying culture flask of large size prepared in advance.

Further, 40 ml of culture medium for cultivation was transferred to new flask and cultivated at 37° C. in the $CO_2$-incubator.

On the 6th day from the commencement of cultivation, 50 ml of culture medium solution was added, and on the 9th day from the commencement of cultivation, 150 ml of culture medium solution was added.

On the 9th day from the commencement of cultivation, the culture solution was transferred from the OKT3-solidifying culture flask to another flask (225 cm(2)) (CELL CULTURE FLASK imported and sold by Corning Coster Japan Corp.).

(3) Aseptic test and endotoxin assay of CD4+ cells:

On the 10th day from the commencement of cultivation, the flask in which the cultivation was done in the aforementioned process (2) was subjected to the aseptic test and endotoxin assey of CD4+ cells in the same manner as that in the process (12) of Embodiment 1 described above. As a result, the flask was confirmed not to be contaminated by any bacterium and the like.

(4) FACS analysis of CD4+ cells for administration before collection:

Before collecting CD4+ cells, FACS analysis was done for the CD4+ cells for administration in the same manner as that in the aforementioned process (13) of Embodiment 1.

As a result, it could be confirmed that the content of CD4+ cells was 99.75%, and the content of CD8+ cells was 0.25%.

(5) Collection of CD4+ cells:

Into a centrifugation tube of 50 ml in capacity, 50 ml of culture solution cultivated in the flask was poured and subjected to centrifugal separation at 1500 rpm at 20° C. for 8 minutes. After the centrifugal separation, supernatant liquid in the centrifugation tube was removed, and then, the tube was stirred by using a vortex to thoroughly loosen cell sedimentum. Next, upon pouring 50 ml of cell-rinsing fluid into the centrifugation tube, the solution was subjected to centrifugal separation at 1500 rpm at 20° C. for 8 minutes. Upon completion of the centrifugal separation, supernatant liquid in the centrifugation tube was removed once more, and stirred by using the vortex to thoroughly loosen cell sedimentum.

Into each of centrifugation tubes, 50 ml of cell-rinsing solution was poured respectively. The cell suspension solution was transferred by 50 ml to each of two tubes of 50 ml in capacity, and then, subjected to centrifugal separation at 1800 rpm at 20° C. for 8 minutes. After the centrifugal separation process, supernatant liquid was removed, and sedimentum of cells was stirred by using a vortex to be thoroughly loosened. Then, to each of tubes of 50 ml in capacity, 10 ml of cell-rinsing fluid was poured respectively.

After the centrifugal separation process, supernatant liquid was removed, and sedimentum of cells was stirred by using a vortex to be thoroughly loosened.

After well suspending the cell suspension in a final solution (solution to be administered to a patient, which is mixed with 200 ml of physiological saline and 20% of human seralbumin in a centrifugation tube of 250 ml in capacity), the solution was filtrated through 100-micron mesh (Product No. 2350 imported and marketed by Nippon Becton Dickinson Co., Ltd.), and then, the quantity of the cell suspension solution was measured.

Further, the cell suspension solution was sampled to measure the number of cells in the solution and the content of CD4.

A 50 ml-syringe was connected to a separation bag T-030 (Product No. BB-T030CJ(300 ml) produced by Terumo Corp.) through a tube to introduce the cell suspension solution into the bag through the syringe. After introduction of the cell suspension solution into the bag, a plunger of the syringe was pressed into the syringe barrel to squeeze out the remaining solution in the syringe, and then, the tube connecting the syringe to the bag was pinched by a forceps and sealed with a tube sealer, consequently to be cut with scissors.

As the result of measurement, the quantity of the solution was 200 ml, and the number of cells in total was $8.0 \times 10^7$.

(6) FACS analysis of CD4+ cells for administration after collection:

After collecting CD+4 cells for administration, FACS analysis was done for the CD4+ cells in the same manner as that in the aforementioned process (15) of Embodiment 1.

As the result of the analysis, the content of CD4+ cells was 99.75%, and the content of CD8+ cells was 0.25%.

(7) Administration of CD4+ cells to a patient:

The CD4+ cells prepared in the aforementioned process (5) were administered to a patient through the vein of the patient over a period of 30 minutes at a rate of $1.0 \times 10^6$ U/kg per patient weight.

[Embodiment 3]

(1) Measurement of blastogenesis reaction of lymphocytes due to PHA and Con-A:

An inspection for blastogenesis reaction of lymphocytes due to PHA and Con-A was entrusted to SRL Inc. The results of the inspection revealed that the blastogenesis reaction of lymphocytes of peripheral blood collected from the patient before administration of CD4+ cells obtained in the process (2) of Embodiment 1 described above was confirmed to be 19098 cpm, but that after administration of CD4+ cells (three weeks after administration) was 38204 cpm. From the result of the inspection, it was found that immunological competence of the patient was increased because of the administration of CD4+ cells.

(2) Measurement of the number of CD4+ cells:

Measurement of the number of CD4+ cells in the peripheral blood was carried out in the following manner.

First, into a tube of 5 ml in capacity, there were poured 100 $\mu$l of total blood and 10 $\mu$l of CD4/CD8 antibodies (T4RD1/T8-FITC 6603802 produced by Coulter Inc.), and then, they were well stirred and reacted 4° C. for 30 minutes.

After reaction, the mixture thus obtained was subjected to hemolysis to be solidified. Upon adding PBS (imported and marketed by GIBCO-BRL Life Technologies Inc.) thereto, it was subjected to centrifugal separation at 6000 rpm for 5 minutes. After rinsing the cells and adding 800 $\mu$l of sheath solution thereto, it was subjected to pipetting to loosen the cells and poured into a FACS-measuring tube (Product No. 2052 imported and sold by Nippon Becton Dickinson Co., Ltd.). As the FACS, COULTER-XL was used.

Although the number of CD4+ cells in the peripheral blood before administration of CD4+ cells as described above on the process (2) of Embodiment 1 was 20 U/$\mu$l, that after administration of CD4+ cells (2 weeks after administration) became 110 U/$\mu$l.

It is evident from this fact that immunological competence of the patient can be increased because of the administration of CD4+ cells.

(3) Detection of cytomegalovirus:

A detection of cytomegalovirus in the peripheral blood was performed by PCR at SRL Inc.

Although cytomegaloviruses were detected before administration of CD4+ cells, no cytomegalovirus was detected 2 weeks after administration of CD4+ cells.

It is evident from this fact that CD4+ cells show antiviral activity in a living body under immunosuppressive condition.

(4) Side effect and clinical observation:

No acute side effect resulting from the administration of CD4+ cells could been confirmed at all.

Four weeks after administration of CD4+ cells, a mysterious rash came out.

Exanthesis which appeared on the patient became erythema and was spread to more than 50% of the whole body, but none of gastrointestinal GVHD nor hepatic GVHD was caused except for a considerably slight grade disease of second grade.

In spite of serious GVHD caused after bone marrow transplantation, the administration of allogenic activated-CD4+ cells did not cause any GVHD essentially encountering a critical problem.

On a bone marrow puncture test conducted 2 weeks after administration, recidivation of leukemia was found out, and on examination of cerebrospinal fluid, central nervous system recidivation was found out, but five weeks after administration, these symptoms went into remission without using carcinostatic.

Further, even after the lapse of two months from administration, no recidivation of leukemia was found out. It is apparent from these facts that allogenic activated-CD4+ cells have excellent antitumor activity.

Besides, the fact that hemophagocytic syndrome disappeared makes it evident that allogenic activated-CD4+ cells are effective against autommune diseases.

As is apparent from the foregoing description, the lymphocytic medicaments and preparations according to the present invention have an extremely beneficial effect for preventing recidivation of a tumor and remedying various infections such as viral infections, and autoimmune diseases such as phagocytosis, without causing any serious GVHD.

As can be readily appreciated, it is possible to deviate from the above embodiments of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A method for treating an infection comprising administering an effective amount of a composition comprising allogenic activated-CD4+ cells as the main ingredient, to the infection.

2. The method for treating an infection as set forth in claim 1, wherein the infection is a viral infection.

3. The method for treating an infection as set forth in claim 1, wherein said composition further comprises a pharmaceutically acceptable carrier or diluent.

4. The method for treating an infection as set forth in claim 1, wherein said allogenic activated-CD4+ cells are derived from an organ or bone marrow transplantation donor.

5. The method for treating an infection as set forth in claim 1, wherein allogenic activated-CD4+ cells is present in an amount of 90% or more based on the total cells in the composition.

6. The method for treating an infection as set forth in claim 1, wherein said composition further comprises activated-CD8+ cells, said activated-CD8+ cells being present in an amount of 10% or less based on the total cells in the composition.

7. The method for treating an infection as set forth in claim 1, wherein said allogenic activated-CD4+ cells are prepared by separating lymphocyte cells or CD4+ cells from peripheral blood of a donor, and proliferating said CD4+ cells prepared.

8. The method for treating an infection as set forth in claim 1, wherein the composition is produced by a method comprising separating CD4+ cells from peripheral blood of a donor, proliferating said CD4+ cells through a proliferation activator to obtain allogenic activated-CD4+ cells, and forming the composition with said allogenic activated-CD4+ cells.

9. The method for treating an infection as set forth in claim 1, wherein said proliferation activator is interleukin-2 and/or anti-CD3 antibodies.

10. The method for treating an infection as set forth in claim 8, wherein said allogenic activated-CD4+ cells are derived from an organ donor or bone-marrow donor.

11. The method for treating an infection as set forth in claim 1, wherein the composition is produced by a method comprising removing CD8+ cells from peripheral blood of a donor via anti-CD8+ antibodies to obtain CD4+ cells, proliferating said CD4+ cells through a proliferation activator to obtain allogenic activated-CD4+ cells, and forming the composition with said allogenic activated-CD4+ cells.

12. The method for treating an infection as set forth in claim 11, wherein said proliferation activator is interleukin-2 and/or anti-CD3 antibodies.

13. The method for treating an infection as set forth in claim 11, wherein said allogenic activated-CD4+ cells are derived from an organ donor or bone-marrow donor.

14. The method for treating an infection as set forth in claim 1, wherein the composition is produced by a method comprising proliferating allogenic lymphocyte cells through a proliferation activator, separating activated-CD4+ cells from said allogenic lymphocyte cells via anti-CD4+ antibodies to obtain allogenic activated-CD4+ cells, and forming the composition with said allogenic activated-CD4+ cells.

15. The method for treating an infection as set forth in claim 14, wherein said proliferation activator is interleukin-2 and/or anti-CD3 antibodies.

16. The method for treating an infection as set forth in claim 14, wherein said allogenic activated-CD4+ cells are derived from an organ donor or bone-marrow donor.

17. The method for treating an infection as set forth in claim 1, wherein the composition is produced by a method comprising proliferating allogenic lymphocyte cells through a proliferation activator, separating activated-CD8+ cells from said allogenic lymphocyte cells via anti-CD8+ antibodies to obtain allogenic activated-CD4+ cells, and forming the composition with said allogenic activated-CD4+ cells.

18. The method for treating an infection as set forth in claim 17, wherein said proliferation activator is interleukin-2 and/or anti-CD3 antibodies.

19. The method for treating an infection as set forth in claim 17, wherein said allogenic activated-CD4+ cells are derived from an organ donor or bone-marrow donor.

* * * * *